(12) United States Patent
Job et al.

(10) Patent No.: US 7,102,012 B2
(45) Date of Patent: Sep. 5, 2006

(54) PROCESS FOR PREPARING N,N'-CARBONYLDIAZOLES

(75) Inventors: Andreas Job, Köln (DE); Bernd Griehsel, Bottrop (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 11/126,535

(22) Filed: May 11, 2005

(65) Prior Publication Data

US 2005/0272937 A1    Dec. 8, 2005

(30) Foreign Application Priority Data

May 13, 2004    (DE)    ............... 10 2004 023 606

(51) Int. Cl.
*C07D 403/06*    (2006.01)
*C07D 233/58*    (2006.01)
*C07D 249/08*    (2006.01)
*C07D 235/04*    (2006.01)
*C07D 403/08*    (2006.01)

(52) U.S. Cl. ............... 548/313.7; 548/341.5; 548/266.6; 548/305.7; 548/365.4

(58) Field of Classification Search ............. 548/313.7, 548/341.5, 266.6, 305.7, 365.4
See application file for complete search history.

(56) References Cited

U.S. PATENT DOCUMENTS 6,392,057 B1    5/2002    Scherer et al. ............ 548/313.7
6,891,045 B1    5/2005    Stamm et al. ............ 548/313.7

FOREIGN PATENT DOCUMENTS

DE    1 033 210        12/1956
EP    0 692 476 B1    7/1994
WO    WO2004-EP13876    * 12/2004

OTHER PUBLICATIONS

"Notiz zur Darstellung von 1.1'-Carbonyl-di-imidazol", Staab, Heinz A., et al, Chem. Ber. 1963, 96, p. 3374.

* cited by examiner

*Primary Examiner*—Joseph K. McKane
*Assistant Examiner*—Yong Chu
(74) *Attorney, Agent, or Firm*—Jennifer R. Seng

(57) ABSTRACT

A process is provided for preparing N,N'-carbonyldiazoles by reacting azoles with phosgene in halogenated aliphatic hydrocarbon solvents, the entirety of the azole for reaction being introduced in the solvent, followed by the addition of phosgene.

14 Claims, No Drawings

PROCESS FOR PREPARING N,N'-CARBONYLDIAZOLES

The present invention relates to an improved process for preparing N,N'-carbonyldiazoles by reacting azoles with phosgene.

It is already known that N,N'-carbonyldiazoles can be obtained by reacting azoles with phosgene (DE-B 10 33 210 and Liebigs Ann. Chem. 1957, 609, 75). In those cases exclusively anhydrous tetrahydrofuran is used in the examples described, with a solution of the entire azole in anhydrous tetrahydrofuran being introduced as the initial charge, and then the phosgene being passed in. The reaction takes place at room temperature. A striking feature is the low concentration of the azole in the THF solvent, of 2% to 4% by weight. In DE-B 1 033 210 it is stated only generally, and without any evidence, that instead of tetrahydrofuran it would in principle also be possible to use other ethers or aliphatic or aromatic hydrocarbons as solvents. In a process described in Chem. Ber. 1963, 96, 3374, similarly, the entire azole is introduced in a THF/benzene solvent mixture and again only concentrations of about 7% by weight of the azole in the solvent mixture are achieved.

According to a more recent process, that of EP-A-692 476, somewhat higher concentrations of the azole in the solvent can be achieved in aromatic solvents such as benzene, toluene, xylenes, chlorobenzenes or mixtures thereof, which are each dewatered by partial distillation prior to reaction, at temperatures of 50 to 120° C. A description is given of concentrations in the range up to 12% by weight. In this case the solvent is first dewatered by partial distillation, then the azole is added and dissolved with heating, and then phosgene is passed in.

WO-A-00/14072 describes a process for preparing carbonyldiimidazole from imidazole and phosgene at a temperature of 60 to 80° C. which is carried out in ortho-, meta- or para-xylene, or mixtures thereof, or in chlorobenzene as solvent and in which the imidazole hydrochloride co-product obtained as a melt is separated from the resultant reaction mixture by phase separation at a temperature of more than 100° C. The reaction per se is carried out by metering phosgene into the initial charge of imidazole solution.

DE-A-198 33 913 discloses a process for preparing N,N'-carbonyldiazoles which operates using aromatic solvents such as benzene, toluene, xylene or chlorinated benzenes which are dewatered beforehand by partial distillation. A key feature of this process is that the azole, in solution in one of the aforementioned aromatic solvents, and phosgene are metered in parallel into a further, initial charge of solvent. A description is given of how by this type of process regime it is possible to achieve an azole concentration of up to 33% by weight. Since, however, a fraction of the solvent used is added together with the reactants, there is no possibility here of subjecting the entire solvent volume to azeotropic drying in the vessel intended for the reaction. Parallel metering is, however, in principle a technique which reduces the economic attractiveness of a process. In this specific case, reasonable filtration of the azole hydrochloride by-product only takes place if a very specific metering ratio is observed precisely. The process, moreover, shows a sensitivity to overphosgenation, leading to a dark coloration of the resulting product.

Not only with the process of DE-A-198 33 913 but also with the other processes described above that use aromatic solvents and run at temperatures of more than 50° C. there is a risk of the azole hydrochloride precipitate formed during the reaction being obtained as a viscous, sticky mass. This mass adheres solidly to vessel walls and stirrer, making it much more difficult to stir the system. The difficulty of the stirring operation limits the maximum possible space/time yield to very low levels. In the case of solidification of the precipitate towards the end of the addition of phosgene, hard balls are formed which may, moreover, cause damage to the reaction vessel and its internals (e.g. stirrer, dip tubes, etc.).

There is therefore a need for an improved process for preparing N,N'-carbonyldiazoles with an extremely simple process regime in which no tacky and problematic azole hydrochloride precipitates occur and, furthermore, no high reaction temperatures are needed that would reduce the economics of the process as a result of high energy costs.

The invention provides a process for preparing N,N'-carbonyldiazoles of the general formula (I)

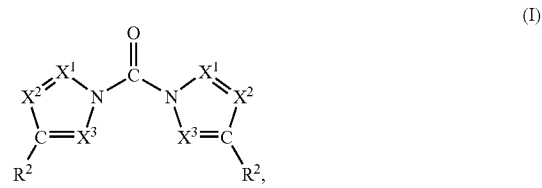

where either $X^1$, $X^2$ and $X^3$ independently of one another are each $CR^1$ or nitrogen, $R^1$ being hydrogen or straight-chain or branched $C_1$–$C_6$ alkyl, and $R^2$ is hydrogen, or $X^1$ and $X^3$ are $CR^1$, the radical $R^1$ in $X^1$ being hydrogen or straight-chain or branched $C_1$–$C_6$ alkyl and the radical $R^1$ in $X^3$ forming, together with $R^2$, a —CH=CH—CH=CH— bridge, and $X^2$ is $CR^1$ or nitrogen, $R^1$ being hydrogen or straight-chain or branched $C_1$–$C_6$ alkyl, by reacting azoles of the general formula (II),

in which the radicals and symbols used have the definitions indicated for the general formula (I), with phosgene, this process being characterized in that (i) a halogenated aliphatic solvent from the group consisting of chlorinated aliphatic hydrocarbons, brominated aliphatic hydrocarbons and mixedly chlorine-/bromine-substituted aliphatic hydrocarbons is used and (ii) in that the entire amount of azole to be reacted is introduced as an initial charge and then phosgene is metered in.

In the process of the invention, in contrast to the processes described in EP-A-692 476, DE-A-198 33 913 and WO-A-00/14072, the azole hydrochloride which precipitates during the reaction, such as the imidazole hydrochloride, for example, is formed and remains continually as a readily stirrable, crystalline precipitate which does not cake or stick to stirrer or vessel walls. Owing to the disperse nature of the precipitate, the stirring resistance is much lower than in the case of a non-inventive mode of operation. Surprisingly, in accordance with the invention, it is possible to obtain much higher reactant concentrations than in the case of the processes known to date, with a comparable non-parallel mode of metering, which results in a significantly improved space/time yield as compared with the prior art: in the case of the processes of EP-A-692476 and WO-A-00/14072 a reactant concentration of 11% and 11.9% by weight in the respective solvent is reported, respectively, whereas with the process of the invention reactant concentrations of up to 25% by weight are obtained. It is also possible to rule out damage to the reactor and its internals as a result of hard azole hydrochloride conglomerates. Furthermore, the process of the invention possesses only very slight sensitivity to overphosgenation, which in other processes leads to discoloration of the isolated product. The quality of the N,N'-carbonyldiazoles thus obtained is therefore distinguished in particular by a very good Hazen colour number.

In the process of the invention it is possible to use either two different azoles or else only one single azole of the general formula (II). In the first case an N,N'-carbonyldiazole of the formula (I) is obtained in which the two azole rings are different. In the second case an N,N'-carbonyldiazole with two identical azole rings is formed. This second procedural variant is the preferred variant.

Preference is further given to using azoles in which in the general formulae (I) and (II) one or two of the moieties $X^1$, $X^2$ and $X^3$ is or are nitrogen. Additionally it is preferred for $X^1$ to be CH, $X^2$ to be nitrogen and $X^3$ to be $CR^1$, $R^1$ and $R^2$ together forming a —CH═CH—CH═CH— bridge.

Particular preference is given to using, in the process of the invention, imidazole, benzimidazole, pyrazole or 1,2,4-triazole as the azole of the general formula (II). Very particular preference is given to imidazole.

The said azoles of the general formula (I) are either available commercially or else are preparable by known processes of the prior art.

It is an essential feature of the process of the invention that the entire amount of the azole of the general formula (II) to be reacted is introduced as an initial charge in the halogenated aliphatic hydrocarbon and then 0.2 to 0.3 mol, preferably 0.22 to 0.28 mol, more preferably 0.25 to 0.27 mol of phosgene is metered in per mole of azole of the general formula (II). Phosgene can here be used in its usual technical grade.

The phosgene can be metered in continuously or semi-batchwise. Continuously here means that the phosgene is metered into the initial charge of azole/solvent mixture permanently at a uniform rate over the entire reaction time. Semi-batchwise means that phosgene is metered into the azole/solvent mixture in portions, distributed over defined time periods.

The halogenated aliphatic solvent to be used originates from the group consisting of chlorinated aliphatic hydrocarbons, brominated aliphatic hydrocarbons and mixedly chlorine-/bromine-substituted aliphatic hydrocarbons.

As chlorinated aliphatic hydrocarbons it is possible for example to use methylene chloride, chloroform, 1,2-dichloroethane, 1,1-dichloroethane or 1,1,2,2-tetrachloroethylene.

As brominated aliphatic hydrocarbons it is possible for example to use bromoform, dibromomethane or 1,2-dibromoethane.

In addition it is possible to use hydrocarbons with mixed chlorine/bromine substitution as solvents, such as 1-bromo-2-chloroethane, for example.

The halogenated aliphatic hydrocarbon from the above-mentioned group that is used as solvent normally possesses a water content of not more than 0.5%, preferably not more than 0.2%, more preferably not more than 0.1% and in particular not more than 0.05% by weight.

Halogenated aliphatic hydrocarbons with this water content are available as solvents either commercially or else by appropriate partial distillation/drying prior to the reaction according to the invention. The latter procedure is appropriate in the process of the invention. In this case it is possible to operate in two variants: on the one hand it is possible first to introduce the entirety of the solvent into the reaction vessel and to carry out partial distillation thereof for the purpose of drying to the desired water content. The entirety of the azole is added thereafter and the phosgene is metered in. On the other hand it is also possible for the entirety of the solvent to be introduced together with the azole in the reaction vessel and for the desired water content to be achieved by partial distillation of the azole/solvent mixture before the phosgene is metered in.

The process of the invention is normally carried out at a temperature in the range from 10 to 100° C., preferably at 20 to 80° C., in particular at 30 to 65° C.

In general it is advantageous, after the phosgene has been metered in, to stir the reaction mixture for a certain time, in the range from 30 minutes to 5 hours, at the same temperature.

In order to remove any excess phosgene present it is possible to pass nitrogen gas through the reaction mixture until phosgene is no longer detectable in the outgoing gas.

Likewise for the purpose of removing any phosgene excesses it is possible for the above-described solvent to be partially distilled until phosgene is no longer detectable in the reaction mixture.

The reaction mixture is worked up by slurrying it from the reaction vessel into a filtration apparatus. Since the azole hydrochloride is in the form of a crystalline precipitate even after the end of the metered addition of phosgene, this slurrying is easy and complete. Then the azole hydrochloride precipitate formed is separated off by filtration at 10 to 100° C., preferably at 20 to 80° C. This filtration as well, owing to the crystalline consistency of the precipitate, is accomplished effectively and within short filtration times. The N,N'-carbonyldiazole can be isolated from the mother liquor obtained during the azole hydrochloride separation by cooling the mother liquor to +40 to −70° C., preferably to +25 to −20° C., and filtering off the product which crystallizes out in the course of cooling. In this way the product is obtained in a well-crystallized form in purities of at least 90%, preferably at least 95%.

It is also possible to concentrate the mother liquor to completion following the azole hydrochloride separation and so to free it from the solvent. The N,N'-carbonyldiazole obtained in this way likewise already possesses a purity of at least 90%, preferably of at least 95%.

The economic attractiveness of the process of the invention can be enhanced if the mother liquor obtained after the crystallized N,N'-carbonyldiazole has been separated off is recycled without further working-up and is used as a basis for the phosgenation of further quantities of azole. This mother liquor may possibly still contain residual fractions of the N,N'-carbonyldiazole. Recycling the mother liquor in this way can be effected a number of times. Surprisingly, very good yields and high purities are still obtained, with no change, and in particular the N,N'-carbonyldiazole obtained using recycled solvent continues to possess the excellent Hazen colour numbers.

A further improvement in the economic attractiveness can be achieved by recovering the quantity of azole obtained as azole hydrochloride in the process of the invention. This azole hydrochloride can be converted back into the free azole and so recycled to the reaction. In this way it is possible to achieve a doubling in the yield of N,N'-carbonyldiazole, based on the azole employed.

The recovery of azoles from azole hydrochlorides can be carried out in accordance with DE-A-198 33 913, for example, by reacting the azole hydrochlorides obtained in the synthesis of the N,N'-carbonyldiazoles with a compound of the formula (III)

M(OR⁴)$_n$                                                              (III), in which
n corresponds to the valency of M,
M is an alkali metal or alkaline earth metal and
R⁴ is hydrogen or $C_1$–$C_4$ alkyl.

This reaction takes place in a solvent mixture composed on the one hand of an aromatic solvent such as, for example, benzene, toluene, a xylene, monochlorobenzene, a dichlorobenzene, a trichlorobenzene or mixtures thereof and, on the other hand, of a solvent of the formula

R⁴OH                                                              (IV), in which
R⁴ has the definition indicated with respect to formula (m).

In the formulae (III) and (IV) R⁴ is preferably hydrogen or methyl, and in formula (III) M is preferably lithium, sodium or potassium.

After the reaction of the azole hydrochloride with the compound of the formula (III) it is advantageous to distil off the entire compound of the formula (IV), including the compound of the formula (IV) formed during the reaction of azole hydrochloride and the compound of the formula (III), to remove the resulting salt $MCl_n$ by filtration at normal or elevated temperature, and to use the azole recovered, following separation of the aromatic solvent, for the N,N'-carbonyldiazole synthesis of the invention.

This procedure goes particularly well if the compound of the formula (III) used is LiOH, NaOH or KOH in a solvent mixture composed of water (which is a compound of the formula (IV) with R⁴=hydrogen) and chlorobenzene, toluene, xylene or 2-methyltetrahydrofuran and if the water is removed by azeotropic distillation, for example, by separating it off on a water separator, or else, if the compound of the formula (III) used is sodium methoxide in a solvent mixture composed of methanol on the one hand and of chlorobenzene or xylene on the other, and if the methanol is separated off by distillation, by, for example, distilling it from the mixture via an effective column.

In summary it is possible with the process of the invention, through the reaction of azole and phosgene using a halogenated aliphatic hydrocarbon solvent selected from the group consisting of chlorinated aliphatic hydrocarbons, brominated aliphatic hydrocarbons and mixedly chlorine- or bromine-substituted aliphatic hydrocarbons, to produce the azole hydrochloride by-product reliably in a non-tacky consistency. This allows the stirring properties of the reaction solution to be improved and hence allows higher concentrations of reactants and correspondingly higher space/time yields to be achieved. At the same time the easy removal of the azo hydrochloride from the reaction vessel is ensured, and damage due to hardened azo hydrochlorides is ruled out. The filtration times as well as filtration are surprisingly short by virtue of the improved filtration characteristics of the azole hydrochloride. A further advantage of the inventive use of a halogenated aliphatic solvent is the very low sensitivity of the reaction system to any excess of phosgene during or at the end of the reaction: as compared with prior art processes, both the consistency of the crystalline azole hydrochloride precipitate and the colour of the N,N'-carbonyldiazole obtained from the reaction mixture are affected little if at all by small excesses of phosgene.

EXAMPLES

The Hazen colour number is determined in accordance with ISO 6271.

Example 1

Inventive

A flask is charged with 531.5 g of dry dichloromethane and 93.8 g (1.37 mol) of imidazole and this initial charge is heated to 35° C. At this temperature over the course of 1.75 hours 36.04 g (0.36 mol) of phosgene are added with an introduction rate of 20.6 g/h. The mixture thus obtained is subsequently stirred at the same temperature for 1.5 h.

In order to ensure a phosgene-free reaction mixture, 13.2 g of distillate are taken off under a pressure of 790 to 500 mbar and at 35–25° C., an ammonia/water/isopropanol mixture is added to the distillate, and this mixture is discarded.

The imidazole hydrochloride by-product (isolated dry weight: 72.1 g) is removed by filtration at 35° C., the filter cake being washed with twice 100 ml of warm dichloromethane at 33° C.

250.1 g of water-clear solution are distilled off from the combined organic phases at 790 to 500 mbar and 35–25° C. The remaining solution is cooled to 0° C., and a suspension forms. The precipitated carbonyl bisimidazole is separated off by filtration and additionally washed with 50 ml of dichloromethane conditioned to a temperature of 0° C.

Drying of the crystals at 4 mbar and 30° C. gives 40.0 g of product in the form of white crystals, Hazen colour number: 69.7. The purity of the product is 99.3%, corresponding to a yield of 71.2% of theory.

Example 2

Comparative in Analogy to Example 1 from WO-A-00/14072

In a flask, 68.22 g of imidazole are suspended in 505 g of xylene. The mixture is heated to reflux and dewatered by taking off 5 g of a xylene/water mixture. The temperature is reduced to 66° C. and over the course of 30 minutes 25.2 g of phosgene are metered in with an introduction rate of 50.4 g/h.

After about 15 minutes the reaction mixture takes on a consistency like that of chewing gum. When the metering of phosgene is at an end the imidazole hydrochloride by-product is in the form of yellow balls. After a further hour of stirring at this temperature, this temperature is raised to 130° C., and the consistency of the imidazole hydrochloride changes to a brown melt.

The melt is drained off at 130° C. It solidifies on cooling to a dark-green, solid mass.

The supernatant xylene phase is cooled to 0° C. The precipitated crystals are filtered off and dried at 20 mbar and 50° C.

This gives carbonylbisimidazole in the form of white crystals with black fractions (Hazen colour number: 489). The purity is 96.8%, corresponding to a yield of 70% of theory.

Example 3

Inventive

A flask is charged with 375.2 g of dry chloroform and 93.8 g of imidazole and this initial charge is heated to 35° C. At this temperature over the course of 1.75 hours 35.02 g of phosgene are added with an introduction rate of 20.0 g/h. The mixture thus obtained is subsequently stirred at the same temperature for 1.5 h.

In order to ensure a phosgene-free reaction mixture, 28 g of distillate are taken off under a pressure of 280 mbar and at 30° C., an ammonia/water/isopropanol mixture is added to the distillate, and this mixture is discarded.

The imidazole hydrochloride by-product (isolated dry weight: 72.1 g) is removed by filtration at 35° C., the filter cake being washed with twice 100 ml of warm chloroform at 35° C.

251.1 g of water-clear solution are distilled off from the combined organic phases at 280 mbar and 30° C. The remaining solution is cooled to 0° C., and a suspension forms. The precipitated carbonyl bisimidazole is separated off by filtration and additionally washed with 50 ml of chloroform conditioned to a temperature of 0° C.

Drying of the crystals at 6 mbar and 30° C. gives 41.5 g of product in the form of white crystals having a Hazen colour number of 44. The purity of the product is 99.5%, corresponding to a yield of 74.0% of theory.

Example 4

Inventive

A flask is charged with 358.1 g of dry chloroform and 119.36 g of imidazole and this initial charge is heated to 55° C. At this temperature over the course of 1.75 hours 44.57 g of phosgene are added with an introduction rate of 25.5 g/h. The mixture thus obtained is subsequently stirred at the same temperature for 2 h.

In order to ensure a phosgene-free reaction mixture, 5.4 g of distillate are taken off under a pressure of 630 mbar and at 35° C., an ammonia/water/isopropanol mixture is added to the distillate, and this mixture is discarded.

The imidazole hydrochloride by-product (isolated dry weight: 96.0 g) is removed by filtration at 55° C., the filter cake being washed with twice 100 ml of warm chloroform at 55° C.

The combined organic phases are cooled to 0° C., and a suspension forms. The precipitated carbonyl bisimidazole is separated off by filtration and additionally washed with 50 ml of chloroform conditioned to a temperature of 0° C.

Drying of the residue at 4 mbar and 46° C. gives 44.3 g of product in crystalline form having a Hazen colour number of 49. The purity of the product is 99.0%, corresponding to a yield of 61.9% of theory.

Example 5

Inventive with Recycling of the Mother Liquor

1st Phosgenation

A flask is charged with 531.5 g of dry dichloromethane and 93.8 g (1.37 mol) of imidazole and this initial charge is heated to 35° C. At this temperature over the course of 1.75 hours 35.02 g (0.35 mol) of phosgene are added with an introduction rate of 20.0 g/h. The mixture thus obtained is subsequently stirred at the same temperature for 1.5 h.

In order to ensure a phosgene-free reaction mixture, 8.4 g of distillate are taken off under a pressure of 750 to 500 mbar and at 35–20° C., an ammonia/water/isopropanol mixture is added to the distillate, and this mixture is discarded.

The imidazole hydrochloride by-product (isolated dry weight: 80.3 g) is removed by filtration at 35° C., the filter cake being washed with twice 100 ml of warm dichloromethane at 33° C.

The remaining solution is cooled to 0° C., and a suspension forms. The precipitated carbonyl bisimidazole is separated off by filtration and additionally washed with 50 ml of dichloromethane conditioned to a temperature of 0° C. After the solid carbonylbisimidazole has been filtered off, 553.0 g of mother liquor M1 are obtained.

Drying of the crystals at 5 mbar and 20° C. gives 33.54 g of product in the form of white crystals with a Hazen colour number of 45.1. The purity of the product is 99.6%. The yield therefore corresponds to 59.9% of theory.

2nd Phosgenation

A flask is charged with 531.5 g of dichloromethane-containing mother liquor M1 from the 1st phosgenation step and 93.8 g (1.37 mol) of imidazole and this initial charge is heated to 35° C. At this temperature over the course of 1.75 hours 35.02 g (0.35 mol) of phosgene are added with an introduction rate of 20.0 g/h. The mixture thus obtained is subsequently stirred at the same temperature for 1.5 h.

In order to ensure a phosgene-free reaction mixture, 21.6 g of distillate are taken off under a pressure of 750 to 450 mbar and at 35–20° C., an ammonia/water/isopropanol mixture is added to the distillate, and this mixture is discarded.

The imidazole hydrochloride by-product (isolated dry weight: 86.6 g) is removed by filtration at 35° C., the filter cake being washed with twice 100 ml of warm dichloromethane at 33° C.

The remaining solution is cooled to 0° C., and a suspension forms. The precipitated carbonyl bisimidazole is separated off by filtration and additionally washed with 100 ml of dichloromethane conditioned to a temperature of 0° C. After the solid carbonylbisimidazole has been filtered off, 553.0 g of mother liquor M2 are obtained.

Drying of the crystals at 6 mbar and 30° C. gives 39.4 g of product in the form of white crystals with a Hazen colour number of 33.2. The purity of the product is 98.7%. The yield therefore corresponds to 70% of theory.

3rd Phosgenation

A flask is charged with 531.5 g of dichloromethane-containing mother liquor M2 from the 2nd phosgenation step and 93.8 g (1.37 mol) of imidazole and this initial charge is heated to 35° C. At this temperature over the course of 1.75 hours 35.02 g (0.35 mol) of phosgene are added with an introduction rate of 20.0 g/h. The mixture thus obtained is subsequently stirred at the same temperature for 1.5 h.

In order to ensure a phosgene-free reaction mixture, 9.2 g of distillate are taken off under a pressure of 750 to 500 mbar and at 35–20° C., an ammonia/water/isopropanol mixture is added to the distillate, and this mixture is discarded.

The imidazole hydrochloride by-product (isolated dry weight: 88.1 g) is removed by filtration at 35° C., the filter cake being washed with twice 100 ml of warm dichloromethane at 33° C.

The remaining solution is cooled to 0° C., and a suspension forms. The precipitated carbonyl bisimidazole is separated off by filtration and additionally washed with 100 ml of dichloromethane conditioned to a temperature of 0° C.

Drying of the crystals at 7 mbar and 20° C. gives 37.3 g of product in the form of white crystals with a Hazen colour number of 41.0. The purity of the product is 98.5%. The yield therefore corresponds to 65.9% of theory.

What is claimed is:

1. A process for preparing N,N'-carbonyldiazoles of the general formula (I)

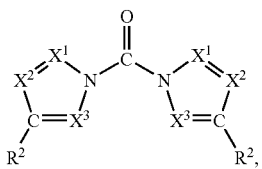

where either
- $X^1$, $X^2$ and $X^3$ independently of one another are each $CR^1$ or nitrogen, $R^1$ being hydrogen or straight-chain or branched $C_1$–$C_8$ alkyl, and
- $R^2$ is hydrogen, or
- $X^1$ and $X^3$ are $CR^1$, the radical $R^1$ in $X^1$ being hydrogen or straight-chain or branched $C_1$–$C_6$ alkyl and the radical $R^1$ in $X^3$ forming, together with $R^2$, a —CH=CH—CH=CH— bridge, and
- $X^2$ is $CR^1$ or nitrogen, $R^1$ being hydrogen or straight-chain or branched $C_1$–$C_8$ alkyl, by reacting azoles of the general formula (II),

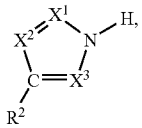

in which the radicals and symbols used have the definitions indicated for the general formula (I), with phosgene, this process being characterized in that
(i) a halogenated aliphatic solvent from the group consisting of chlorinated aliphatic hydrocarbons, brominated aliphatic hydrocarbons and mixedly chlorine-/bromine-substituted aliphatic hydrocarbons is used and
(ii) in that the entire amount of azole to be reacted is introduced as an initial charge and then phosgene is metered in.

2. The process according to claim 1, wherein either two different azoles or else only one single azole of the general formula (II) are or is used.

3. The process according to claim 1, wherein one or two azoles of the general formula (II) is or are used in which independently of one another one or two of the moieties $X^1$, $X^2$ and $X^3$ is or are nitrogen.

4. The process according to claim 1, wherein one or two azoles of the general formula (II) is or are used in which independently of one another $X^1$ is CH, $X^2$ is nitrogen and $X^3$ is $CR^1$, $R^1$ and $R^2$ together forming a —CH=CH—CH=CH— bridge.

5. The process according to claim 1, wherein imidazole, benzimidazole, pyrazole or 1,2,4-triazole is used as the azole of the general formula (II).

6. The process according to claim 1, wherein 0.2 to 0.3 mol of phosgene is used per mole of azole of the general formula (II).

7. The process according to claim 1, wherein the chlorinated aliphatic hydrocarbons used are methylene chloride, chloroform, 1,2-dichloroethane, 1,1-dichloroethane and 1,1,2,2-tetrachloroethylene.

8. The process according to claim 1, wherein the brominated aliphatic hydrocarbons used are bromoform, dibromomethane or 1,2-dibromoethane.

9. The process according to claim 1, wherein a mixedly chlorine-/bromine-substituted hydrocarbon used is 1-bromo-2-chloroethane.

10. The process according to claim 1, wherein the solvent possesses a water content of not more than 0.5%.

11. The process according to claim 1, wherein the solvent used is dried by partial distillation optionally in the presence of the azole.

12. The process according to claim 1, wherein the reaction mixture is worked up by separating off the azole hydrochloride precipitate at 10 to 100° C., by filtration and isolating N,N'-carbonyldiazole from the filtrate by cooling the mother liquor to +40 to −70° C., and filtering off the N,N'-carbonyldiazole that crystallizes out in the course of cooling.

13. The process according to claim 12, wherein the mother liquor obtained after the N,N'-carbonyldiazole has been separated off is recycled without further working-up and is used for the phosgenation of further quantities of an azole of the general formula (II).

14. The process according to claim 12, wherein after the phosgenation the reaction mixture is worked up by separating off the azole hydrochloride precipitate at 20 to 80° C. by filtration as indicated in claim 12 and concentrating the filtrate completely and thereby removing the solvent.

* * * * *